United States Patent [19]

Goto et al.

[11] Patent Number: 5,149,651
[45] Date of Patent: Sep. 22, 1992

[54] PROCESS FOR CULTURING MICROORGANISMS OF THE GENUS PSEUDOMONAS AND PROCESS FOR PRODUCING L-ALANINE USING SAID MICROORGANISMS

[75] Inventors: Makoto Goto, Inashiki; Terukazu Nara, Niihari; Yasukazu Uchida, Inashiki; Masato Terasawa, Inashiki; Hideaki Yukawa, Inashiki; Hisashi Yamagata, Ushiku, all of Japan

[73] Assignee: Mitsubishi Petrochemical. Co., Ltd., Tokyo, Japan

[21] Appl. No.: 691,880

[22] Filed: Apr. 26, 1991

[30] Foreign Application Priority Data

Apr. 27, 1990 [JP] Japan .................. 2-110272
Mar. 18, 1991 [JP] Japan .................. 3-52528

[51] Int. Cl.$^5$ .................. C12N 1/38; C12N 1/36; C12R 1/38; C12P 13/06
[52] U.S. Cl. .................. 435/244; 435/42; 435/116; 435/232; 435/245; 435/253.6; 435/874; 435/876; 435/877
[58] Field of Search .................. 435/244, 245, 42, 116, 435/253.6, 232, 874, 876, 877

[56] References Cited

U.S. PATENT DOCUMENTS 3,458,400 1/1968 Chibata et al. .
5,019,509 5/1991 Rozzell .................. 435/116

FOREIGN PATENT DOCUMENTS 0386476 9/1990 European Pat. Off. ............ 435/116
53-27355 8/1978 Japan .
53-27792 8/1978 Japan .
0039759 3/1980 Japan .................. 435/116
60-19997 5/1985 Japan .
0087088 4/1987 Japan .................. 435/116
2207794 8/1990 Japan .................. 435/116
2242690 9/1990 Japan .................. 435/116
3047084 2/1991 Japan .................. 435/116
1059668 2/1967 United Kingdom .

OTHER PUBLICATIONS

Chemical Abstracts, vol. 83, No. 25, Dec. 22, 1975, p. 122, abstract No. 202918e.
Patent Abstracts of Japan, vol. 1, No. 54, May 25, 1977, p. 374 C 77; & JP-A-52 012 983 Jan. 31, 1977 & JP-B-53 027 355 Aug. 8, 1978.

*Primary Examiner*—Herbert J. Lilling
*Attorney, Agent, or Firm*—Sughrue, Mion, Zinn, Macpeak & Seas

[57] ABSTRACT

Microorganisms of the genus Pseudomonas containing aspartate beta-decarboxylase at a high level are produced by culturing said microorganism in a medium supplemented with a chelating agent. L-Alanine can be efficiently produced from L-aspartic acid said microorganisms or the treated product thereof.

11 Claims, No Drawings

PROCESS FOR CULTURING MICROORGANISMS OF THE GENUS PSEUDOMONAS AND PROCESS FOR PRODUCING L-ALANINE USING SAID MICROORGANISMS

BACKGROUND OF THE INVENTION

1. Field of the Invention

The invention relates to a process for culturing microorganisms of the genus Pseudomonas containing aspartate beta-decarboxylase and to a process of producing L-alanine using said microorganisms.

Aspartate beta-decarboxylase is a useful enzyme for enzymatic production of L-alanine. L-Alanine, as is well known in the art, is an important amino acid as a starting material for pharmaceuticals, foods, or as a chemical industry raw materials. The demand therefore has been rapidly increasing in recent years.

2. Description of the Related Art

Although it has been proposed to culture microorganisms containing aspartate beta-decarboxylase with lactic acid and pyruvic acid added to the medium (Japanese Patent Publication No. 19997/1985) or with L-glutamic acid added to the medium (Japanese Patent Publication No. 27355/1978), the organic and amino acids are costly.

As an industrial process for producing L-alanine, there has been proposed a process for producing L-alanine through enzymatic decarboxylation of L-aspartic acid (Japanese Patent Publication No. 27792/1978). However, the enzyme content in the microoganisms used in that process is low.

SUMMARY OF THE INVENTION

The purpose of the present invention is to provide a process for culturing microorganisms of the genus Pseudomonas containing aspartate beta-decarboxylase, according to which microorganism cells containing aspartate beta-decarboxylase at a high level can be obtained using a medium at a moderate cost, and to provide a process for producing L-alanine from L-aspartic acid at high efficiency using said microorganisms.

The present inventors, as a result of earnest research in an endeavor to achieve the above-mentioned purposes, accomplished the invention by discovering that microorganism cells containing a markedly increased content of aspartate beta-decarboxylase could be obtained if said microorganism is cultivated in a medium supplemented with a chelating agent.

According to the present invention, there is provided a process for culturing microorganisms of the genus Pseudomonas, which comprises a process for culturing microorganisms of the genus Pseudomonas containing aspartate beta-decarboxylase, characterized in that cultivation is carried out in a medium supplemented with a chelating agent, and a process for producing L-alanine from L-aspartic acid using said microorganisms or treated products thereof.

DESCRIPTION OF THE PREFERRED EMBODIMENTS

As microorganisms used in the present invention, any microorganisms belonging to the genus Pseudomonas and containing aspartase beta-decarboxylase can be used. For example, there can be included *Pseudomonas dacunhae* ATCC 21192, *Pseudomonas putida* ATCC 21812, *Pseudomonas fluorescens* IFO 3081, and *Pseudomonas syringae* IFO 3310. Those strains are preferred.

Among these microorganisms, *Pseudomonas dacunhae* ATCC 21192 and *Pseudomonas putida* ATCC 21812 have been deposited at the American Type Culture Collection, 12301 Parklawn Drive, Rockville, Md. 20852, U.S.A. *Pseudomonas fluorescens* IFO 3081 and *Pseudomonas syringae* IFO 3310 have been deposited at the Institute for Fermentation, Osaka, 17–85, Juso-honmachi, Yodogawa-ku, Osaka 532, Japan. The microorganisms are freely available to the public.

As a medium used for preparation of microorganism cells containing aspartate beta-decarboxylase, any medium having been commonly utilized can be used, but the invention is characterized in that a chelating agent is present in the medium.

As chelating agents that can be added to the medium, any chelating agent forming a chelate with metal ions in the medium can be used. For example, ethylenediamine tetraacetic acid (EDTA), ethyleneglycol-bis (2-aminoethyl) tetraacetic acid (EGTA), hydroxyethylenediamine triacetic acid (HEDTA), diethylene-triamine-penta-acetic acid (DTPA), nitrilotriacetate (NTA), or triethylenetetramine hexaacetic acid (TTHA), the salts thereof, or o-phenanthroline may be appropriately used.

Concentration of a chelating agent in the medium is usually 0.001 to 5 g/l, preferably 0.005 to 2 g/l. The optimal concentration range differs according to the kind of chelating agent used; they are, for example, 0.1–2 g/l for EDTA, 0.05–0.5 g/l for HEDTA and TTHA, and 0.005–0.05 g/l for o-phenanthroline.

As to the timing of adding the chelating agent to the medium, it can be added before or after initiation of cultivation, but it is desirable to add it by the middle of the exponential growth phase of cultivation.

Although there are not particular limitations on the carbon source for the medium used for preparation of the microorganism cells containing aspartate beta-decarboxylase, fumaric acid, succinic acid, and aspartic acid can be mentioned. Among these acids, fumaric acid preferably is used.

As the nitrogen source for the medium, an inorganic salt, such as ammonia, ammonium sulfate, ammonium chloride, ammonium nitrate and urea, can be used as well as an organic nutrient source, such as peptone, yeast extract, corn steep liquor and casamino acids.

As the inorganic salt, there can be used dipotassium hydrogen phosphate, potassium dihydrogen phosphate, and magnesium sulfate.

Cultivation of the microorganism cells containing aspartate beta-decarboxylase is carried out under aerobic conditions, such as aeration, stirring or shaking, and the cultivation temperature may be 20° to 40° C., preferably 28° to 32° C. The pH in the course of cultivation may be 5 to 10, preferably around 7 to 8, and is adjusted with addition of an acid or an alkali. The fumaric acid concentration at the initiation of cultivation may be preferably 0.01 to 5% (wt/vol), more preferably 0.05 to 2% (wt/vol). The length of cultivation may be 8 hours to 4 days, preferably 10 hours to 2 days.

Since the microorganism cells obtained through cultivation according to the above-mentioned process contain a large amount of asparatate beta-decarboxylase in their cells, L-alanine can be efficiently produced from L-aspartic acid by means of enzymatic reaction in an aqueous reaction solution using said microorganism cells or the treated product thereof.

The treated product of microorganism cells herein means the disrupted product of the cells obtained through destruction of the cells using a known method, such as sonication treatment and squeezing, the immobilized product of the cells or said disrupted product obtained by a known method, such as immobilization with such a monomer as acrylamide or with alginic acid.

Next, as an adaptation of the present invention, the process for producing L-alanine from L-aspartic acid by means of enzymatic reaction in aqueous reaction solution using the above-mentioned microorganism cells or the treated product thereof is described below.

The concentration of L-aspartic acid or the salt thereof that may be added to the aqueous reaction solution is 0.5 to 50% (wt/vol), preferably 3 to 30% (wt/vol). In addition, L-aspartic acid can be present in either dissolved form or as a powder (undissolved form) in relation to the solubility of L-aspartic acid in the reaction solution.

Said aqueous reaction solution can be used with addition of pyridoxal 5'-phosphate at 0.0005 to 0.05% (wt/vol), preferably 0.001 to 0.01% (wt/vol). If necessary, the aqueous reaction solution can be also used with additional supplementation of a nonionic surfactant, such as polyoxyethylene (10) octyl phenylether and polyoxyethylene (20) sorbitan monolaurate, at 0.01 to 0.5% (wt/vol), preferably 0.03 to 0.2% (wt/vol).

If necessary, an alpha-keto acid, such as pyruvic acid and alpha-ketobutyric acid, can be added to said aqueous reaction solution at 0.001 to 0.5% (wt/vol), preferably 0.01 to 0.2% (wt/vol).

The pH in the course of enzymatic reaction may be 4.5 to 5.3, preferably 4.8 to 5.0, the reaction temperature may be 30° to 47° C., preferably 37° to 42° C., and the reaction is usually carried out for about 3 to 48 hours. For adjustment of the pH of the reaction solution, an alkaline aqueous solution, such as an ammonia solution, sodium hydroxide solution and potassium hydroxide solution, may be preferably used.

Separation and purification of L-alanine formed in the reaction solution obtained according to the above-mentioned reaction method can be practiced by a known method, such as ion exchange resin treatment and crystallization.

The present invention will be more specifically described in reference to the following examples.

In the following examples, the activity of aspartate beta-decarboxylase was determined by measuring an amount of alanine formed after microorganism cells collected from 100 ml of the culture medium were suspended in 200 ml of reaction solution (containing 1500 mM aspartic acid, 0.04 mM pyridoxal 5'-phosphate, 5 mM pyruvic acid, 0.1% (vol/vol) polyoxyethylene (10) octyl phenylether, and 0.4M ammonia; pH 4.8) and shaken at 37° C. for 1 hour.

L-Alanine was qualitatively confirmed with the Rf value in paper chromatography, the retention time of high performance liquid chromatography, and specific rotation of the purified product. Quantitative analysis was performed on high performance liquid chromatography (Shimazu LC-5A). In the following actual examples, the representation % means % (wt/vol) unless otherwise mentioned.

EXAMPLE 1

Culturing of Microorganisms

A culture medium at 100 ml (containing 0.5% sodium fumarate, 1.0% ammonium fumarate, 1.0% corn steep liquor, 0.05% potassium dihydrogen phosphate, and 0.05% $MgSO_4 \cdot 7H_2O$; pH, 7.0) was apportioned into an Erlenmeyer flask of 500 ml volume, and after sterilization, *Pseudomonas dacunhae* ATCC 21192 was inoculated and incubated at 30° C. for 1 day while being shaken (preliminary cultivation).

Next, one liter each of the same culture medium as that mentioned above, which was supplemented with one of the chelating agents shown in Table 1 at the concentration shown in Table 1, was charged into a 2-liter volume tank operated under aeration stirring, and after sterilization (120° C., 20 minutes), 20 ml of the above-mentioned cultured product was added. After that, cultivation was carried out under rotation at 100 rpm, at an aeration amount of 1 vvm, a temperature of 30° C., and a pH of 7.3 for 1 day.

After completion of the cultivation, 100 ml each of all of the cultured products were centrifuged to collect cells, said cells were washed in 0.9% NaCl solution, and then the activity of aspartate beta-decarboxylose in said washed cells was measured by the above-mentioned method.

As Comparative Example 1, the same procedure was performed without addition of any chelating agent to the medium.

The results are illustrated in Table 1.

TABLE 1

| Test No. | Chelating agent | Concentration | Relative activity of L-aspartate beta-decarboxylase* |
|---|---|---|---|
| (Example 1) | | | |
| 1 | ethylenediamine tetraacetic acid (EDTA) | 1.0 g/l | 220 |
| 2 | hydroxyethylene-diamine triacetic acid (HEDTA) | 0.25 g/l | 145 |
| 3 | triethylene-tetramine hexaacetic acid (TTHA) | 0.25 g/l | 160 |
| 4 | o-phenanthroline | 0.02 g/l | 140 |
| (Comparative Example) 1 | not added | | 100 |

*Relative value to the activity of L-aspartate beta-decarboxylase in the comparative example, which was regarded as 100.

EXAMPLE 2

Culturing of Microorganisms

The same procedure as that used in Example 1 was performed, other than that *Pseudomonas fluorescens* IFO 3081 was used as a bacterial strain, and ethylenediamine tetraacetic acid was added at 0.5 g/l.

As Comparative Example 2, the same procedure as that used in Example 2 was performed without addition of ethylenediamine tetraacetic acid to the medium.

The results are illustrated in Table 2.

TABLE 2

| | Relative activity of L-aspartate beta-decarboxylase* |
|---|---|
| Example 2 | 160 |
| Comparative Example 2 | 100 |

*Relative value to the activity of L-aspartate beta-decarboxylase in the comparative example, which was regarded as 100.

EXAMPLE 3

Culturing of Microorganisms

The same procedure as that used in Example 1 was performed, other than that *Pseudomonas syringae* IFO 3310 was used as a bacterial strain, and ethylenediamine tetraacetic acid was added at 0.5 g/l.

As Comparative Example 3, the same procedure as that used in Example 3 was performed without addition of ethylenediamine tetraacetic acid to the medium.

The results are illustrated in Table 3.

TABLE 3

| | Relative activity of L-aspartate beta-decarboxylase* |
|---|---|
| Example 3 | 155 |
| Comparative Example 3 | 100 |

*Relative value to the activity of L-aspartate beta-decarboxylase in the comparative example, which was regarded as 100.

EXAMPLE 4

Production of L-alanine

According to the same method as that used in Example 1, *Pseudomonas dacunhae* ATCC 21192 was cultured in the medium supplemented with ethylenediamine tetraacetic acid at 1.0 g/l. After 100 ml of the cultured product was centrifuged to collect cells, the cells were washed in 100 ml of 0.9% NaCl solution, and all of the yielding cells were suspended in 200 ml of aqueous reaction solution [containing 30% L-aspartic acid, 0.05% (vol/vol) polyoxyethylene (10) octyl phenylether, 0.001% pyridoxal 5'-phosphate, and 0.05% sodium pyruvate; pH, 4.7 (adjusted with ammonium solution containing $NH_3$ at 28%)] and shaken at 42° C. for 5 hours. After that, the yield of L-alanine was measured.

As Comparative Example 4, the same procedure was performed without addition of ethylenediamine tetraacetic acid to the medium. Their results are illustrated in Table 4.

TABLE 4

| | Relative yield of cells* | Yield of L-alanine (g/l) |
|---|---|---|
| Example 4 | 97 | 155 |
| Comparative Example 4 | 100 | 71 |

*Relative value to the yield of cells in the comparative example, which was regarded as 100.

We claim:

1. A process for culturing microorganisms of the genus Pseudomonas containing aspartate beta-decarboxylase comprising cultivating said microorganisms in a medium comprising a chelating agent selected from the group consisting of ethylenediamine tetraacetic acid (EDTA), ethyleneglycol-bis (2-aminoethyl) tetraacetic acid (EGTA), hydroxyethylenediamine triacetic acid (HEDTA), diethylenetriaminepentaacetic acid (DTPA), nitrilotriacetate (NTA), triethylenetetraamine hexaacetic acid (TTHA), the salts thereof and o-phenanthroline, wherein the chelating agent concentration in the medium is 0.001 to 5 g/l.

2. The process of claim 1, wherein said microorganisms are selected from the group consisting of *Pseudomonas dacunhae* ATCC 21192, *Pseudomonas putida* ATCC 21812, *Pseudomonas fluorescens* IFO 3081 and *Pseudomonas syringae* IFO 3310.

3. The process of claim 1 or 2, wherein cultivation of microorganisms is carried out under aerobic conditions at a temperature of 20° to 40° C., at a pH of 5 to 10, for a period of 8 hours to 4 days.

4. The process of claim 1 or 2, wherein cultivation of microorganisms is carried out in the presence of fumaric acid at 0.01 to 5% (wt/vol).

5. The process of claim 1, wherein said concentration is 0.005 to 2 g/l.

6. The process of claim 3, wherein said temperature is 28° to 32° C.

7. The process of claim 3, wherein said pH is 7 to 8.

8. The process of claim 3, wherein said period is 10 hours to 2 days.

9. The process of claim 3, wherein cultivation of microorganisms is carried out in the presence of fumaric acid at 0.01 to 5% (wt/vol).

10. The process of claim 9, wherein said fumaric acid is present at 0.05 to 2% (wt/vol).

11. The process of claim 4, wherein said fumaric acid is present at 0.05 to 2% (wt/vol).

* * * * *